US008449897B2

(12) United States Patent
Whitmire et al.

(10) Patent No.: US 8,449,897 B2
(45) Date of Patent: *May 28, 2013

(54) REFRESHMENT TOWEL AND APPLIED SOLUTION

(76) Inventors: A. Jeffrey Whitmire, Canton, GA (US); Mona L. Whitmire, Canton, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/465,696

(22) Filed: May 7, 2012

(65) Prior Publication Data

US 2012/0219646 A1   Aug. 30, 2012

Related U.S. Application Data

(63) Continuation of application No. 12/208,944, filed on Sep. 11, 2008, now Pat. No. 8,182,826.

(60) Provisional application No. 60/971,436, filed on Sep. 11, 2007.

(51) Int. Cl.
*A61K 8/02* (2006.01)
*A61K 36/00* (2006.01)

(52) U.S. Cl.
USPC .......................................... 424/401; 424/725

(58) Field of Classification Search
USPC ................................. 424/401, 725
See application file for complete search history.

(56) References Cited

U.S. PATENT DOCUMENTS

| 5,858,330 | A  | * | 1/1999 | Boltri et al. ...................... 424/45 |
| 8,182,826 | B2 | * | 5/2012 | Whitmire et al. .............. 424/401 |
| 2002/0165286 | A1 | * | 11/2002 | Hedeman et al. .............. 514/785 |
| 2005/0002974 | A1 | * | 1/2005 | Filbry et al. .................. 424/401 |
| 2005/0249805 | A1 | * | 11/2005 | Holsztynska ................. 424/464 |
| 2007/0123691 | A1 | * | 5/2007 | Wilson .......................... 528/374 |

OTHER PUBLICATIONS

Associated Press: An Astrological Guide to Scent; Toronto Star; Toronto, Ont., Dec. 29, 2005, p. E05, pp. 1-2 of ProQuest database print-out.*
Harari et al. What'S New; Jerusalem Post; jERUSALEM; Jun. 25, 2004, p. 05, pp. 1-4 of ProQuest database print-out.*

* cited by examiner

*Primary Examiner* — Patricia Leith
(74) *Attorney, Agent, or Firm* — Smith Risley Tempel Santos LLC; Gregory Scott Smith

(57) ABSTRACT

A refreshment towel with applied solution is an apparatus consisting of a carrying agent, most likely a high quality cotton towel or towelette, that has been saturated with an aqueous solution comprised of various ingredients. The resulting saturated towel can be rubbed on a user's skin such that the aqueous solution that has been absorbed by the towel is transferred. The aqueous solution is compounded specifically to provide cooling, insect repellant, sun protection, freshness, cleansing and other uses. More specifically, the aqueous solution is specially formulated so that desired sensory results take place when the towel comes in contact with the skin.

9 Claims, 2 Drawing Sheets

REFRESHMENT TOWEL AND APPLIED SOLUTION

CROSS-REFERENCE TO RELATED APPLICATIONS

This document, filed under 35 USC 111 and 37 CFR 1.53(b) as a continuation of the United States Patent Application that was filed on Sep. 11, 2008, bearing the title of REFRESHMENT TOWEL AND APPLIED SOLUTION, assigned Ser. No. 12/208,944 and issued as U.S. Pat. No. 8,182,826 on May 22, 2012, which patent claims the benefit of the filing date of the United States Provisional Application for Patent that was filed on Sep. 11, 2007 and assigned Ser. No. 60/971,436

BACKGROUND OF THE INVENTION

It's hot, dang hot! Africa hot! Tarzan couldn't take this kind of heat! This paraphrase of probably the only memorable quote from the movie Biloxi Blues needs no explanation, especially if you have ever tried to accomplish anything outdoors in a southern state in the middle of the summer heat. We have all experienced moments where this quote could be used. Whether on the golf course, sitting in a baseball stadium, sitting on the sidelines while your child is playing soccer, mowing the grass, an outdoor wedding, changing a flat tire, or the like, there are just times that are almost unbearable.

However, if you are an outdoors type of person and you refuse to be imprisoned in your nice air-conditioned home by the summer heat, you most likely have had, and will have, moments when you simply need some relief. People have found themselves in these situations time and time again. Hence, a typical scene in western movies is a sweat drenched, dusty cowboy dunking his head into the horse trough to cool down. This may seem like a refreshing step but, if you have ever raised horses, you will appreciate that a horse trough is certainly no place to be sticking your head. In fact, choosing between the options of a heat stroke or sticking your face into the slimy, grime that floats around in a horse trough is a tough call.

Other, less dramatic techniques have also been employed such as, seeking the shade of a tree, building a fan by folding a piece of paper, putting a cold beverage to your forehead, running through the water sprinklers, retreating to an air-conditioned room, stepping in front of a fan, or wetting a towel to put over the back of your neck.

The human body also has its own solution—sweat glands (or if you are a lady, glow glands). It is well known that as a liquid evaporates, it helps to eradicate heat. This is the purpose of your sweat—it helps to keep your body cool. As sweat evaporates from the surface of your skin, excess heat is removed and as a result, you are cooled. This phenomenon is based on the principle in physics which basically states that a certain amount of heat needs to be applied to a liquid in order for that liquid to evaporate—pass from a liquid form to a vaporous or gaseous form. This amount of heat is referred to as the heat of vaporization. The basis of this principle is that as the heat energy increases the speed of the water molecules also increase. Once the speed of the water molecules reaches a certain speed, they can escape into the air. The heat energy for this process is provided by your body. Thus, the heat used to evaporate sweat is then used up which in turn operates to cool your body down.

This all works quite well in a nice dry environment, however, when you are in a highly humid environment, things begin to break down. First of all, the air in a highly humid environment is already near saturation and thus, cannot absorb much additional water vapor. Thus, the sweat cannot evaporate and you remain hot, and now, a sweaty mess.

The troubles one finds in the heat of the summer don't stop there. First of all, as bacteria on your skin mixes with your sweat, you begin to emit noxious odors. Furthermore, the bugs and insects that once would hit and bounce off of you now have a tendency to hit and stick.

Trying to stay in such conditions is not only a matter of comfort. As salt and sodium exits your body in your sweat, you can quickly dehydrate which can lead to circulatory problems and heat stroke. It is important to ensure that you do not overheat, especially in hot humid environments. Thus, there is a need in the art for a device to assist in the cooling down of an individual.

Because many of the activities that occur outside are athletic in nature, it is not convenient to carry around products typically necessary to help a person stay cool, such as fans, ice, etc. Thus, there is a need in the art for a device that is compact, easy to carry and assists in the cooling down of an individual. Further, corporate and promotional events are often centered around outdoor activities such as a golf tournament, a concert, or a resort. Consequently, there is a need for corporate sponsors to offer their invitees an inexpensive, sanitary, and convenient way to cool off, repel insects, and stay productive while capitalizing on the opportunity to build and enhance brand awareness through a simultaneous dissemination of a trademark, banner, or logo.

Other issues that arise in the summer outdoors can also be a nuisance. For instance, if you go too far south in the state of Georgia, you cross the well known Gnat Line. Below the Gnat Line one is constantly attacked by what some refer to as the Confederate Air Force designed to keep the Yankees away. The fact of the matter is, however, that in the southern states, insects are more prevalent. And to further exasperate matters, most insects, especially gnats, are attracted to moisture. As a result, your sweaty face gets bombarded by a host of gnats. It would be of great benefit to have a device that not only cools a person down but that also could help to alleviate the nuisance from insects. Moreover, while gnats are truly annoying, a device with an insect repellant property is even more desirable when one considers the need to keep more sinister insects at bay, such as mosquitoes, which are prone to carrying and transmitting disease.

In addition, as the world gets educated on the dangers of exposing your skin to the ultraviolet light of the sun, products with an associated Sun Protection Factor (SPF) have grown in popularity. Applying SPF rated products to the skin is imperative if you are working outdoors and prone to getting sunburns. Thus, it would be beneficial for a cooling device to also provide the application of an SPF rated product to the skin.

Part of feeling refreshed obviously includes smelling fresh. Thus, it would be beneficial for a cooling device to also provide a fresh scent to an individual.

Also, because many people have skin prone to drying and cracking, it would be beneficial for a cooling device to provide a means of skin rehydrating and softening.

The various embodiments, features and aspects of the present invention, either by themselves or in conjunction with each other, address each of these needs in the art, as well as other needs in the art as described herein.

BRIEF SUMMARY OF EMBODIMENTS OF THE INVENTION

A refreshment towel with applied solution is an apparatus consisting of a carrying agent, most likely a high quality cotton towel or towelette, that has been saturated with an aqueous solution comprised of various ingredients. The resulting saturated towel can be rubbed on a user's skin such that the aqueous solution that has been absorbed by the towel is transferred. The aqueous solution is specially formulated so that desired sensory results take place when the towel comes in contact with the skin. One aspect of embodiments of the present invention is the aqueous solution, or the specific combinations thereof.

In a preferred embodiment, the specially formulated aqueous solution contains, among other ingredients, a concentration of menthol and alcohol. The presence of the menthol and alcohol creates a cooling sensation to the user when it is applied to the skin. Additionally, menthol and alcohol are well documented as sterilization agents having anti-bacterial properties. Advantageously, a towel soaked in such a solution provides a means of cooling off without having to douse oneself with water, go inside where the air is conditioned, or just shed clothes. Further, the optional inclusion of essential oils and additives, in addition to the menthol and alcohol, can offer additional desirable properties such as sanitation, skin softening and moisturizing, fragrance, invigoration, alertness, relaxation, etc.

Moreover, a quality towel can be weaved, stitched or embroidered to include a logo or other similar decorative items for the purpose of marketing and promotional giveaways. Additionally, embodiments of the invention can be easily packaged and stored until ready for use, after which the remainder is a useful towel or cloth product suited for everyday use.

The uses for the various embodiments of the present invention are virtually limitless and quite varied. Almost universally, anybody in need of physically cooling off can make use of an embodiment of the present invention. Whether a person is just passing the time sitting on the back porch during a hot, balmy summer night, or dug in deep in a foxhole somewhere in the blistering Middle East while serving this great country, the present invention affords a convenient, compact, safe and sanitary way to get some relief from the heat, improve hygiene, or stay alert. Women suffering from "hot flashes" or in the throws of labor, hospital patients in need of physical comfort, missionaries spreading the Gospel in the hot, remote, bug infested corners of the earth, government workers and volunteers working to rebuild disaster areas, men and women of the armed forces exposed to the elements while selflessly defending our freedom, all can benefit from various embodiments of the present invention.

DETAILED DESCRIPTION OF THE INVENTION

Figure 1:
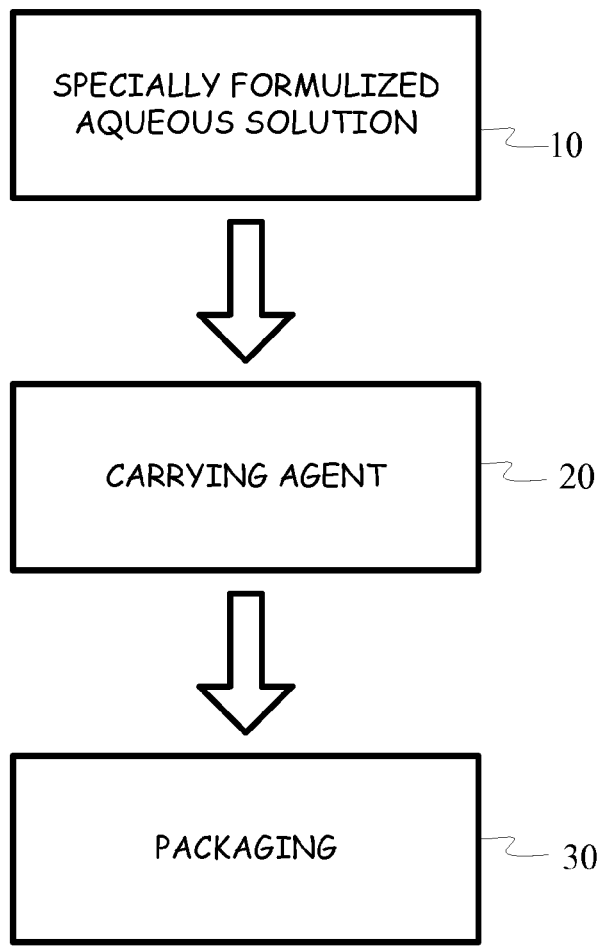
FIG. 1 is a three dimensional block diagram intended to represent an exploded view of the components making up an exemplary embodiment of the present invention.

The present invention, as well as features and aspects thereof, is directed towards providing a towel, or towelette, that is moistened with a solution which when applied to the body, can help to cool the body, warm the body, refresh the body and provide other beneficial effects as well.

In general, embodiments of the present invention operate to help a subject, such as a person or animal, to stay cool, alert, relaxed, refreshed, and free from, or at least less bothered by, the pestering and biting of insects. In addition, some embodiments of the present invention can be used as promotional items for organizations and businesses to build brand awareness and loyalty by putting their customized logo on the embodiments of the invention, or the packaging thereof, and giving them away after different events and as gifts-awards. Furthermore, embodiments of the present invention have the added benefit of being suitable for other purposes after providing refreshment and cooling to the subject.

More specifically, an exemplary embodiment of the present invention is in the form of a towel or other form of cloth that is soaked in a natural solution. The natural solution includes various ingredients to meet various needs or alleviate various problems. For instance, one embodiment of the present invention may include a carrying agent that is cloth-like in nature and fabricated from natural fibers including, but not limited to, 100% cotton, bamboo fabric, or even a non-woven material, and saturated or moistened with a specially formulated aqueous solution containing natural products. It should be appreciated that one skilled in the art may choose any material capable of absorbing the aqueous solution, for the purpose of acting as a carrying agent. Once the cloth, or carrying agent, has been saturated with the aforementioned solution, the solution can be applied to a user by simply rubbing the cloth on the skin. Depending on the particular formulation of the aqueous solution, application to the user's skin can operate to perform one or more of the functions in the following non-limiting list:

removing heat calories from the body;
cooling the body down;
providing a refreshing feeling;
soothing a person;
helping to awaken or keep a person alert;
opening skin pores to enable the body to breathe better and cool more quickly;
preventing insects from biting and pestering;
moisturizing the skin so that it does not dry out;
leaving a fresh scent;
cleaning body parts; and/or
sanitizing body parts or surfaces.

Preferred embodiments of the present invention employ cotton towels as the carrying agent for the specially formulated aqueous solution. Cotton is a desirable natural fiber for use as the carrying agent because it is readily attainable, all natural, hypoallergenic, absorbent and recyclable. Further, a cotton carrying agent can be kept cool, cold, or frozen. It holds an aqueous solution extremely well and has long term holding ability without degradation. Further, a cotton carrying agent, such as a towel, potentially has long term appeal for usability by an end user as it may be employed for other uses once the aqueous solution it carries has been exhausted. Alternative uses for the towel after its initial purpose is a benefit for such a product when used for promotional purposes. For instance, the towel could be used as a golf towel, a wash cloth, dry towel, etc. Thus, it should be clear that embodiments that use a quality towel actually provide a dual use.

As an alternative to cotton, bamboo fiber is used as a carrying agent in some embodiments of the present invention. One aspect of the present invention when using bamboo fiber as a carrying agent is the added benefit of enhanced absorption capacity. Bamboo has on the order of four times the absorption capacity of cotton and, therefore, is capable of carrying larger quantities of the aqueous solution. Consequently, a carrying agent made of bamboo fiber performs longer for its intended purpose as a carrying agent of the aqueous solution. Further, benefits of bamboo fiber as a carrying agent include the aspect that bamboo fiber has natural anti-bacterial agents useful for sanitation purposes. Also, bamboo affords a user natural UV protection. Advantageously, it is softer than cotton and is comparable in feel to cashmere or silk. In addition, similar to cotton, bamboo is environmentally friendly and a renewable resource. It can be kept cool or frozen. It holds an aqueous solution very well and has long term holding power without degradation. Finally, like cotton, a carrying agent made of bamboo fiber has long term appeal for usability by the end user.

A towel made from natural fibers is the preferred carrying agent for a specially formulated aqueous solution that, when applied to an end user, can operate to impart a desirable sensation or condition. It should be noted that the present invention is not limited to the particular carrying agent, although the particular carrying agent may be considered novel in and of itself. For instance, the carrying agent may even include a nonwoven material, a squeeze bottle, a roll-on type bottle, a moisture stick delivery system such as a deodorant stick, or a spray-on bottle.

One aspect of embodiments of the present invention is the essential oils and liquid mixture, herein called a specially formulated aqueous solution, coupled with a convenient delivery system, that benefit the user wishing to transfer or apply a solution to the skin.

The present invention makes use of a standard foundational mixture from which various embodiments of the specially formulated aqueous solution may be achieved based on subsequent additions of essential oils and other ingredients. The foundational mixture common to most embodiments of the specially formulated aqueous solution is comprised of the following ingredients:

Purified Water 70% to 95%
Polysorbate 20 (CAS #9005-64-5) as solubiliser from 3% to 0.005%
L-Menthol (CAS #89-78-1) as cooling agent from 4% to 0.005%
Ethyl Alcohol (CAS #64-17-5) as solubiliser/cooling agent from 3% to 0.005%
Isopropyl Alcohol (CAS #200-661-7) as Denaturant for ethyl alcohol from 3% to 0.005%
Peg-6 Caprylic/Capric Glycedires (CAS #127281-18-9) Co-Solubiliser 1.5% to 0.005%
Glycerine (CAS #56-81-5) Moisturizer 3% to 0.005%
Phenagon PDI (Phenoxyethanol+DMDM Hydantoin+Iodoprophyl Butylcarbamat) Preservative 2.5% to 0.002%
Or
Phenonip (Phenoxyethanol+Methylparabens+Ethylparabens+Prophylparabens+Butylparabens) Preservative 3% to 0.002%

The variations in percent concentrations for the ingredients of the foundational mixture to the aqueous solution are necessary to accommodate choices of subsequent custom additions and carrying agent characteristics. Advantageously, one ingredient of the foundational mixture is a natural moisturizer, glycerine, and serves to offset possible drying effects stemming from the presence of alcohols and menthols used to create cooling sensations or alleviate bacteria. Further, another standard ingredient found in the foundational mixture of the aqueous solution that is a component of the present invention, is a preservative used, advantageously, to give the invention a minimum two year shelf life when stored per the manufacturer's instructions.

Once the foundational mixture has been formulated, additional ingredients are added in order to concoct an aqueous solution designed to deliver specific sensations to an end user. An exemplary formula of these subsequent additions to the foundational mixture includes the following elements:

Lemon Grass Oil (CAS #8007-02-1) Essential oil (insect repellant, and refreshing) 5% to 0.005%
Citronella Oil (CAS #8000-29-1) Essential oil (insect repellant, and refreshing) 5% to 0.005%
Bergamot Oil (CAS #8000-75-8) Essential oil (invigorating and refreshing) 5% to 0.005%
Grapefruit Oil (CAS #8016-20-4) Essential oil (refreshing, cleaning, & fragrance) 5% to 0.003%

The four additional ingredients in the exemplary additive solution outlined immediately above are dissolved in the foundational mixture described prior in order to create a specially formulated aqueous solution. The particular exemplary solution described thus far operates to not only cool an individual when applied to his or her skin (menthol and alcohol), but also to moisturize the skin (glycerine), generate a pleasant fragrance (Lemon Grass Oil, Citronella Oil, Bergamot Oil, Grapefruit Oil), and provide a degree of protection of insects (Lemon Grass Oil, Citronella Oil).

Another aspect of embodiments of the present invention is the relative ease and safety of the application process whereby the specially formulated aqueous solution is transferred from the carrying agent to the skin of the user. Such an aspect is particularly beneficial when considered in light of the exemplary specially formulated aqueous solution described above, which contains elements included as a result of the insect repellent properties. More specifically, because the present invention affords the means to wipe insect repellent on the skin in a targeted fashion, these embodiments of the present invention avoid the need to use c spray-based delivery systems. Advantageously, natural ingredients with insect repellent properties that are used by the present invention can be safely applied to the face in a careful, targeted manner, unlike spray or squirt-based applicators that can cause insect repellent formulas to get into the eyes, ears, nose, and mouth. However, the various aqueous solutions may also be formulated for placement into a spray bottle or other delivery mechanisms if so desired.

Other exemplary mixtures of additive ingredients combined with the foundational formula can create a specially formulated aqueous solution capable of treating a wide number of conditions or providing desirable effects including, but not limited to, relief from hot flashes, relief from sweat flashes, mitigation of foul odor, cleansing and sanitization of skin, changing of mood, and relief from stress. Further, various embodiments of the present invention may employ aqueous solution combinations designed to relax, calm, invigorate, raise awareness, heighten focus, or combat fatigue. Various combinations of the specially formulated aqueous solution component of the present invention may include any one, or a combination of, the elements listed below in addition to the elements outlined in the exemplary formula above:

Peppermint Oil (CAS #68917-18-0) Essential Oil (refreshing and fragrance), 5% to 0.003%
Tangerine Oil (CAS #8008-31-9) Essential oil (refreshing, cleaning, & fragrance), 5% to 0.003%
Lime Oil (CAS #8008-26-2) Essential oil (refreshing, cleaning, & fragrance), 5% to 0.003%
Eucalyptus Citriodora Oil (CAS #8000-48-4) Essential Oil (refreshing, winter time, and fragrance), 4% to 0.003%
Eucalyptus Chinese Oil (CAS #68917-18-0 Essential Oil (refreshing, winter time, and fragrance), 4% to 0.003%
Grapefruit Oil (CAS #8016-20-4) Essential oil (refreshing, cleaning, & fragrance), 5% to 0.003%
Lavender Oil (CAS#008000-28-0) Essential oil (refreshing & fragrance), 5% to 0.002%
Lemon Oil (CAS #84929-31-7) Essential oil (refreshing, cleaning, & fragrance), 5% to 0.003%

Orange Oil (CAS #8028-48-6) Essential Oil (refreshing, cleaning, & fragrance), 5% to 0.003%

Tea Tree Oil (CAS #85085-48-9) Essential oil (refreshing, invigorating & fragrance), 5% to 0.003%

Vanilla Oil Essential oil (CAS#008024-06-4) (refreshing, invigorating & fragrance), 5% to 0.003%

Green Tea Oil Essential oil (CAS#999999-34-7) (refreshing, invigorating & fragrance), 5% to 0.003%

Geranium Oil (CAS #8000-46-2) Essential Oil (refreshing and fragrance), 4% to 0.003%

Spearmint Oil (CAS #8007-02-1) Essential oil (refreshing and fragrance), 5% to 0.005%

Mandarin Oil (CAS #8008-31-9) Essential oil (refreshing, cleaning, & fragrance), 5% to 0.003%

Coconut oil monoglycerides, ethoxylated (CAS#068553-03-7) Synonyms: Glycerides, coco mono-, ethoxylated; Coconut oil monoglycerides, ethoxylated, 5% to 0.003%

Coconut diethylamide (CAS #068603-42-9) Synonyms: Coconut diethylamide; Coconut diethanolamide (1); Aldanolamide; Amides, coco, N,N-bis(2-hydroxyethyl); Coconut oil acid diethanolamine, 5% to 0.003%

Coconut fatty acids (CAS#061788-47-4) Synonyms: Acids, coconut; Coco fatty acid; Coconut acid; Coconut fatty acids; Coconut oil acids; Fatty acids, coco, 5% to 0.003%

Cocoamidopropylbetaine (CAS#061789-40-0) Synonyms: Cocoamidopropyl betaine; N-(Coco alkyl) amido propyl dimethyl betaine; Coconut oil amidopropyl betaine; Quaternary ammonium compounds, (carboxymethyl)3-cocoamidopropyl) dimethyl, hydroxides, inner salts; 1-Propanaminium, 3-amino-N-(carboxymethyl)-N,N-dimethyl-, N-coco acyl derivs., inner salts, 5% to 0.003%

Cucumber extract (CAS#089998-01-6) Synonyms: Cucumber extract; Cucumis sativus extract, 5% to 0.003%

Vanilla oil/extract (CAS#008024-06-4) Synonyms: Protovanol; Oils, vanilla; Vanilla extract, 5% to 0.003%

Green tea (CAS#999999-34-7), 5% to 0.003%

Lavender oil (CAS#008000-28-0) Synonyms: Lavender oil; Lavandula officinalis oil; Lavender flowers oil; Oil of lavender; Oils, lavender, 5% to 0.003%

Coconut oil, diethanolamine condensate (Surfactant) (CAS#008051-30-7) Synonyms: Surfactants (2); Coconut oil diethanolamine condensate; Coconut oil, reaction products with diethanolamine, 5% to 0.003%

Yet another embodiment of the present invention may include an aqueous solution formulation that contains an ingredient with an associated Sun Protection Factor (SPF) designed to protect a user's skin against UVA and UVB radiation. Because an advantage of the present invention is to cool the body when applied to the skin, it is logical that typical users of the present invention may often be exposed to hot, sunny outdoor conditions. Advantageously, a formulation of the aqueous solution component of the present invention that contains an ingredient with an associated SPF, in addition to the cooling agents, would provide an added bonus of a much needed additional level of protection.

Turning now to the figures in which like references refer to like elements throughout the several views, various aspects and embodiments of the present invention are further described.

FIG. 1 is a three dimensional block diagram intended to represent an exploded view of the present invention in a typical embodiment. As described above, the specially formulized aqueous solution 10 is a combination of the previously outlined foundation mixture in conjunction with additional additives present for desired effects including, but not limited to, insect repellent, SPF quality, and fragrance. The specially formulized aqueous solution 10 is applied to a carrying agent 20 until the carrying agent 20 reaches a point of saturation. Once saturated with the specially formulized aqueous solution 10, the carrying agent 20 is hermetically sealed in a packaging solution 30 capable of preventing the specially formulized aqueous solution 10 from evaporating out of the carrying agent 20. In an exemplary embodiment, this packaging can be of superior quality to ensure resistance against evaporation, introduction of bacteria and mold, and operates to provide an extended shelf life. The carrying agent 20 in the preferred embodiment depicted in the figure may be a cloth-like structure constructed of any number of natural fibers including, but not limited to, cellulose, cotton, bamboo, wood products, grass products, or even spray bottles, squeeze bottles, etc. Further, the carrying agent 20 may be of a non-woven form, a knitted form, a woven form, or any other form known to those skilled in the art of cloth manufacture. It must be appreciated that depending upon the particular formulation of the aqueous solution 10, the size of the carrying agent 20, the material of construction for the carrying agent 20 and other specific embodiment factors, the optimum carrying agent 20 gram weight may vary. For example, the preferred range of cloth weight for a woven carrying agent 20 made of cotton and used as a component in the present invention is 22 to 55 grams for a one square foot cloth. The ideal weight, within that range, for the same carrying agent 20 would be roughly 30 grams+/−10%. To further the example, a carrying agent 20 made of cotton that was of a knitted construction and measuring two and a quarter square feet ideally has a weight range of 70 to 85 grams.

Figure 2:
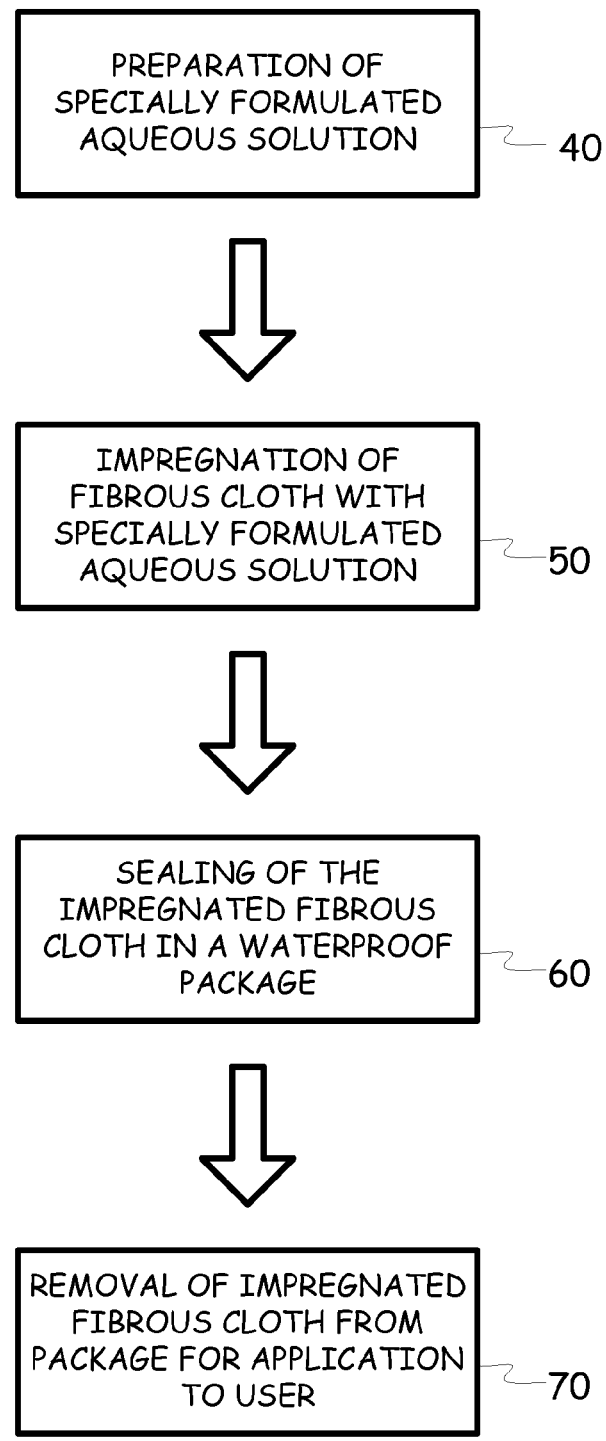
FIG. 2 is a block flow chart diagram depicting an exemplary method of manufacture for a typical embodiment of the present invention.

Moving now to FIG. 2, the method of manufacture for the present invention is depicted via a block flow chart. As described prior, typical embodiments of the specially formulated aqueous solutions 10 contain a foundational mixture containing a measure of purified water, polysorbate, 1-menthol, ethyl alcohol, isopropyl alcohol, a moisturizer and preservatives. The preparation 40 of the specially formulated aqueous solution 10 entails combining the foundational mixture with at least one of the essential oils or additives listed prior in this specification. Components in the foundational mixture serve as solvents for the essential oils or additives and enable the creation of the homogenous mixture that is the aqueous solution 10. Once the aqueous solution 10 has been prepared 40, it is impregnated 50 into a fibrous cloth carrying agent 20 until the cloth is saturated with the solution 10. After impregnation 50 of the carrying agent 20 is complete, the product is then sealed 60 in a waterproof package 30 that prevents evaporation of the aqueous solution 10. The presence of preservatives in the foundational mixture of the aqueous solution 10 combined with the sealed, waterproof packaging 30 provide a means by which the product can be stored for up to two years without degradation of quality. The method is complete when the product is removed 70 from the packaging 30 and applied to the user.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

Further, it will be appreciated by persons skilled in the art that the present invention is not limited by what has been particularly shown and described herein above. Rather, the scope of the invention is defined by the claims that follow.

What is claimed is:

1. A kit for applying at least one of a variety of treatments to a subject, the kit comprising:
   a base aqueous solution comprising:
   70% to 95% purified water by volume;
   0.005% to 3% ethyl alcohol by volume;
   0.005% to 3% isopropyl alcohol by volume;
   0.005% to 3% polysorbate 20 by volume;
   0.005% to 4% 1-menthol by volume;
   0.005% to 1.5% peg-6 caprylic glycerides by volume;
   0.005% to 3% glycerine by volume;
   and further comprising of the elements of:
   0.005% to 5% lemon grass oil and 0.005% to 5% citronella oil (CAS#8000-29-1) to provide the specialized treatment of insect repelling;
   0.002% to 3% phenonip as a preservative to provide extended shelf life;
   0.003% to 5% mandarin oil by volume;
   0.005% to 5% bergamot oil by volume; and
   0.003% to 5% grapefruit oil by volume.

2. A kit for applying at least one of a variety of treatments to a subject, the kit comprising:
   a base aqueous solution comprising:
   70% to 95% purified water by volume;
   0.005% to 3% ethyl alcohol by volume;
   0.005% to 3% isopropyl alcohol by volume;
   0.005% to 3% polysorbate 20 by volume;
   0.005% to 4% 1-menthol by volume;
   0.005% to 1.5% peg-6 caprylic glycerides by volume;
   0.005% to 3% glycerine by volume;
   and further comprising of the elements of:
   0.002% to 3% phenonip as a preservative to provide extended shelf life; and
   0.005% to 5% bergamot oil by volume;
   0.003% to 5% mandarin oil by volume; and
   0.003% to 5% grapefruit oil by volume.

3. The kit of claim 2, further comprising:
0.005% to 5% lemon grass oil.

4. The kit of claim 2, further comprising:
0.005% to 5% citronella oil.

5. The kit of claim 2, further comprising:
0.005% to 5% lemon grass oil; and
0.005% to 5% citronella oil.

6. The kit of claim 2, further comprising:
0.005% to 5% cucumber extract by volume.

7. The kit of claim 3, further comprising:
0.005% to 5% green tea oil essential by volume.

8. The kit of claim 2, further comprising:
0.005% to 5% vanilla oil essential oil by volume.

9. The kit of claim 2, further comprising:
0.005% to 5% lavender essential oil by volume.

* * * * *